(12) United States Patent
Kihara et al.

(10) Patent No.: US 10,134,185 B2
(45) Date of Patent: Nov. 20, 2018

(54) ENDOSCOPIC SURGERY ASSISTING SYSTEM USING HEAD-MOUNTED DISPLAYS AND ASSOCIATED METHODOLOGY

(71) Applicants: SONY CORPORATION, Tokyo (JP); TOKYO MEDICAL AND DENTAL UNIVERSITY, Tokyo (JP)

(72) Inventors: Kazunori Kihara, Tokyo (JP); Tomoyuki Oki, Kanagawa (JP)

(73) Assignee: SONY CORPORATION, Tokyo (JP)

( * ) Notice: Subject to any disclaimer, the term of this patent is extended or adjusted under 35 U.S.C. 154(b) by 86 days.

(21) Appl. No.: 14/651,415

(22) PCT Filed: Dec. 6, 2013

(86) PCT No.: PCT/JP2013/007183
§ 371 (c)(1),
(2) Date: Jun. 11, 2015

(87) PCT Pub. No.: WO2014/103193
PCT Pub. Date: Jul. 3, 2014

(65) Prior Publication Data
US 2015/0317830 A1 Nov. 5, 2015

(30) Foreign Application Priority Data
Dec. 27, 2012 (JP) .................. 2012-284273

(51) Int. Cl.
| | |
|---|---|
| *G06T 19/00* | (2011.01) |
| *A61B 1/00* | (2006.01) |
| *G06F 3/01* | (2006.01) |
| *G02B 27/01* | (2006.01) |
| *G06T 3/40* | (2006.01) |
| *A61B 6/00* | (2006.01) |
| *A61B 8/00* | (2006.01) |

(52) U.S. Cl.
CPC ........ *G06T 19/003* (2013.01); *A61B 1/00006* (2013.01); *A61B 1/00009* (2013.01);
(Continued)

(58) Field of Classification Search
None
See application file for complete search history.

(56) References Cited

U.S. PATENT DOCUMENTS 5,558,619 A * 9/1996 Kami ................ A61B 1/00006
600/106
5,836,869 A 11/1998 Kudo et al.
(Continued)

FOREIGN PATENT DOCUMENTS

| JP | 7-327921 A | 12/1995 |
|---|---|---|
| JP | 8-206083 A | 8/1996 |

(Continued)

OTHER PUBLICATIONS

International Search Report dated Jan. 28, 2014 in PCT/JP2013/007183.

*Primary Examiner* — David D Davis
(74) *Attorney, Agent, or Firm* — Oblon, McClelland, Maier & Neustadt, L.L.P.

(57) ABSTRACT

An endoscopic system according to an embodiment of the present technology includes a head-mounted display, a detector, and a controller. The head-mounted display is worn by an operator. The detector is capable of detecting a motion of the operator. The controller causes each of the plurality of head-mounted displays to individually display an image. The controller includes an endoscopic image acquisition unit capable of obtaining endoscopic image data of an affected area of a patient and an image control unit capable of controlling the endoscopic image data based on an output from each of the plurality of detectors. The controller performs control to display the image based on an output from the image control unit.

18 Claims, 9 Drawing Sheets

(52) U.S. Cl.
CPC ...... *A61B 1/00045* (2013.01); *A61B 1/00048* (2013.01); *A61B 6/462* (2013.01); *A61B 8/462* (2013.01); *G02B 27/0172* (2013.01); *G06F 3/012* (2013.01); *G06T 3/40* (2013.01); *G06T 2207/10004* (2013.01); *G06T 2207/10081* (2013.01); *G06T 2207/10132* (2013.01); *G06T 2207/30004* (2013.01)

(56) References Cited

U.S. PATENT DOCUMENTS

| | | | | |
|---|---|---|---|---|
| 2001/0006376 | A1* | 7/2001 | Numa | G02B 27/017 345/7 |
| 2005/0156817 | A1* | 7/2005 | Iba | G02B 27/0093 345/8 |
| 2011/0234484 | A1* | 9/2011 | Ogawa | A61B 1/00039 345/156 |

FOREIGN PATENT DOCUMENTS

| | | |
|---|---|---|
| JP | 9-28663 A | 2/1997 |
| JP | 9-98985 A | 4/1997 |
| JP | 10-174673 A | 6/1998 |
| JP | 10-309258 A | 11/1998 |
| JP | 2000-60876 A | 2/2000 |
| JP | 2001-104246 A | 4/2001 |
| JP | 2004-267634 A | 9/2004 |
| JP | 2011-112828 A | 6/2011 |
| JP | 2011-145488 A | 7/2011 |
| JP | 2012-223363 A | 11/2012 |

* cited by examiner

ENDOSCOPIC SURGERY ASSISTING SYSTEM USING HEAD-MOUNTED DISPLAYS AND ASSOCIATED METHODOLOGY

TECHNICAL FIELD

The present technology relates to an endoscopic surgery assisting system including a head-mounted display and to an image control method using this system.

BACKGROUND ART

Endoscopic surgery is less invasive to a patient in comparison with general surgery and has been recently popular. In the endoscopic surgery, an operator or the like checks an affected area using images, and hence it is sometimes difficult to stereoscopically grasp the affected area using conventional two-dimensional images. In view of this, for example, a head-mounted display (HMD) capable of providing three-dimensional images is connected to an endoscopic apparatus and used such that more precise and speedy endoscopic surgery can be performed while viewing realistic images of the affected area with a stereoscopic effect (see Patent Document 1).

By the way, during endoscopic surgery, the operator or the like may refer to other diagnosis images such as an ultrasonic image as well as endoscopic images. Thus, when using the HMD for endoscopic surgery, there is a need for providing a configuration in which the operator or the like can view not only the endoscopic images displayed on the HMD but also the other diagnosis images displayed on an external monitor or the like. In view of this, for example, Patent Documents 2 and 3 each describe an HMD whose display is placed in only a part of a field of view such that an outside can be seen through a region other than the display. In addition, Patent Document 4 describes an HMD that ensures that an outside can be seen by rotating a mirror or the like that displays images to left and right eyes.

Patent Document 1: Japanese Patent Application Laid-open No. 2011-145488
Patent Document 2: Japanese Patent Application Laid-open No. 2000-060876
Patent Document 3: Japanese Patent Application Laid-open No. HEI 8-206083
Patent Document 4: Japanese Patent Application Laid-open No. 2011-112828

SUMMARY OF INVENTION

Problem to be Solved by the Invention

However, with the HMD described in each of Patent Documents 2 and 3, the outside can always be seen. Therefore, it is difficult to concentrate on endoscopic images displayed on the display of the HMD. Further, with the HMD described in Patent Document 4, it is necessary to manually rotate the mirror for ensuring that the outside can be seen. Therefore, it is difficult for an operator who needs to keep the hands clean during surgery to touch the mirror for appropriately consulting other diagnosis images and the like.

In view of the above-mentioned situation, it is an object of the present technology to provide an endoscopic surgery assisting system and an image control method, by which an endoscopic image or the like displayed on an HMD can be controlled according to a motion of an operator.

Means for Solving the Problem

In order to achieve the above-mentioned object, an endoscopic surgery assisting system according to an embodiment of the present technology includes a head-mounted display, a detector, and a controller.

The head-mounted display is worn by an operator.

The detector is worn by an operator and capable of detecting an motion of the operator.

The controller causes the head-mounted display to display an image.

The controller includes an endoscopic image acquisition unit that is capable of obtaining endoscopic image data of an affected area of a patient and an image control unit that is capable of controlling the endoscopic image data based on an output from the detector and performs control to display the image based on an output from the image control unit.

With the endoscopic surgery assisting system, it becomes possible to control an image displayed on a head-mounted display (HMD) based on a motion of the operator. With this, without using hands that should be kept clean, it becomes possible to cause the HMD to display an endoscopic image and other diagnosis images that should be consulted during surgery according to the operator's own intention.

The detector may be mounted on the head-mounted display.

With this, an additional mounting tool or the like for mounting the detector on the operator becomes unnecessary and the configuration can be simplified.

The head-mounted display may include a plurality of head-mounted displays that are worn by a plurality of persons including the operator, and the controller may cause the plurality of head-mounted displays to display images based on the output from the image control unit.

With this, based on a motion of the operator, it is possible for a plurality of persons wearing HMDs to check the same image and perform a surgical operation. Thus, all the persons wearing the HMDs can share information. It contributes to sophistication, increased safety, and efficient education of the surgical operation.

The image control unit may judge, based on the output from the detector, whether or not an image switching motion is performed by the operator and switch, if it is judged that the image switching motion is performed, output image data to image data corresponding to the image switching motion.

With this, it is possible to cause the HMD to display various images according to image switching motions.

The image control unit may judge, based on the output from the detector, whether or not a control start motion is performed by the operator and validate a judgment result relating to the image switching motion if it is judged that the control start motion is performed.

With this, it is possible to prevent images from being switched based on motions during surgery irrespective of the operator's intention.

The endoscopic surgery assisting system may further include a notification unit that notifies, if the image control unit validates the judgment result relating to the image switching motion, a wearer of the validation of the judgment result.

With this, it becomes possible for the wearer to know the fact that the image switching motion is valid.

The controller may further include a ultrasonic image acquisition unit that is capable of obtaining ultrasonic image data on the affected area. An image control unit may then judge, based on the output from a detector, whether or not an ultrasonic image switching motion is performed by the operator, and switch output image data from the endoscopic image data to the ultrasonic image data if the ultrasonic image switching motion is performed. Alternatively, the image control unit may include a CT image acquisition unit that is capable of obtaining CT image data on the affected area. The image control unit may judge, based on the output from the detector, whether or not a CT image switching motion is performed by the operator and switch output image data from the endoscopic image data to the CT image data if the CT image switching motion is performed. With this, during the endoscopic surgery, it is possible to consult the ultrasonic image or the CT image without largely moving the line of sight. This makes it possible to reduce fatigue of the operator and perform a more sophisticated surgical operation.

That is, the image data corresponding to the image switching motion can be either the ultrasonic image data or the CT image data associated with the affected area of the patient that is displayed using the endoscopic image.

After the controller causes the head-mounted display to display the CT image, the image control unit may judge, based on the output from the detector, whether or not a viewpoint changing motion is performed by the operator, and switch a viewpoint of the CT image displayed based on the viewpoint changing motion. Alternatively, the image control unit may judge, based on the output from the detector, whether or not a magnification changing motion is performed by the operator, and switch a magnification of the endoscopic image displayed based on the magnification changing motion. This makes it possible to accurately grasp the condition of the affected area according to the operator's intention, allowing for a more precise and speedy surgical operation.

That is, the image data corresponding to the image switching motion may be image data in which a viewpoint of the image that the controller causes the head-mounted display to display is changed based on the output from the detector.

Alternatively, the image data may be image data in which a magnification of the image that the controller causes the head-mounted display to display is changed based on the output from the detector.

The head-mounted display may include a casing that can be placed in front of an eye of the operator; a display surface that is supported by the casing and presents the image to the operator; and an opening that is formed in the casing and provides the operator with a field of view at hand. This makes it possible for the operator to obtain the field of view at hand through the opening, and to more smoothly use other small rigid tools (forceps, scissors, tweezers, etc.)

In order to achieve the above-mentioned object, an endoscopic surgery assisting system according to an embodiment of the present technology includes a plurality of head-mounted displays, a plurality of detectors, and a controller.

The plurality of head-mounted displays are worn by a plurality of persons including an operator.

The plurality of detectors are worn by the plurality of persons and capable of detecting motions of the plurality of persons.

The controller causes each of the plurality of head-mounted displays to individually display an image. The controller includes an endoscopic image acquisition unit that is capable of obtaining endoscopic image data of an affected area of a patient and an image control unit that is capable of controlling each piece of the endoscopic image data based on an output from each of the plurality of detectors and performs control to display the image based on an output from the image control unit.

With this, each of the persons wearing the HMDs can control displayed images according to the intention of each person. With this, it becomes possible to share a work therebetween and make the surgical operation efficient.

In order to achieve the above-mentioned object, an image control method according to an embodiment of the present technology includes a step of monitoring an output from a detector that is capable of detecting a motion of an operator wearing a head-mounted display.

Whether or not an image switching motion is performed by the operator is judged based on the output from the detector.

If it is judged that the image switching motion is performed, endoscopic image data output to the head-mounted display is switched to image data corresponding to the image switching motion.

The image control method may further include judging, based on the output from the detector and prior to judging whether the image switching motion is performed, whether or not a control start motion is performed by the operator. The image control method also includes validating a judgment result relating to the image switching motion if it is judged that the control start motion is performed.

The step of judging whether or not the image switching motion is performed may include judging, based on the output from the detector, whether or not the ultrasonic image switching motion is performed by the operator. The step of switching the endoscopic image data may include a step of switching, if it is judged that the ultrasonic image switching motion is performed, endoscopic image data output to the head-mounted display to the ultrasonic image data.

The step of judging whether or not the image switching motion is performed may include judging, based on the output from the detector, whether or not the CT image switching motion is performed by the operator. The step of switching the endoscopic image data may include a step of switching, if it is judged that the CT image switching motion is performed, the endoscopic image data output to the head-mounted display to CT image data.

The image control method may further include judging, based on the output from the detector and after the step of switching the endoscopic image data to the CT image data, whether or not a viewpoint changing motion is performed by the operator. The image control method may further include switching, if it is judged that the viewpoint changing motion is performed, a viewpoint of the CT image based on the viewpoint changing motion.

The step of judging whether or not the image switching motion is performed may include judging, based on the output from the detector, whether or not the magnification changing motion is performed by the operator. The step of switching the endoscopic image data may include a step of switching, if it is judged that the magnification changing motion is performed, a magnification of the endoscopic image based on the magnification changing motion.

Effect of the Invention

As described above, according to the present technology, it is possible to provide an endoscopic surgery assisting system, by which an image displayed on an HMD can be controlled according to a motion of an operator.

BRIEF DESCRIPTION OF DRAWINGS

FIG. 3 A cross-sectional view of an HMD shown in FIG. 1, which is worn by an operator or the like.

MODE(S) FOR CARRYING OUT THE INVENTION

Hereinafter, embodiments according to the present technology will be described with reference to the drawings.

<First Embodiment>
[Endoscopic Surgery Assisting System]

Figure 1:
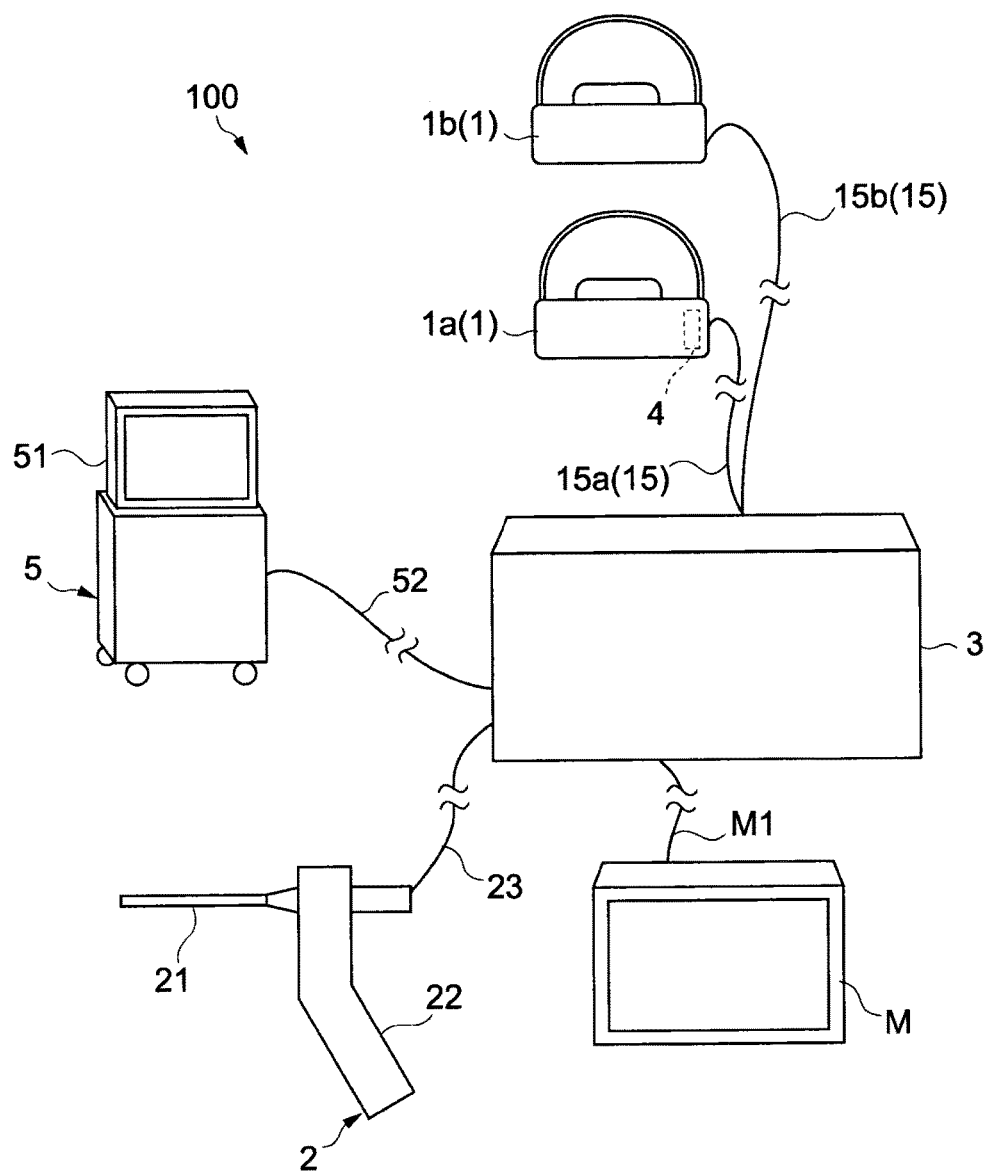
FIG. 1 A schematic view showing a configuration of an endoscopic surgery assisting system according to a first embodiment of the present technology.
Figure 2:
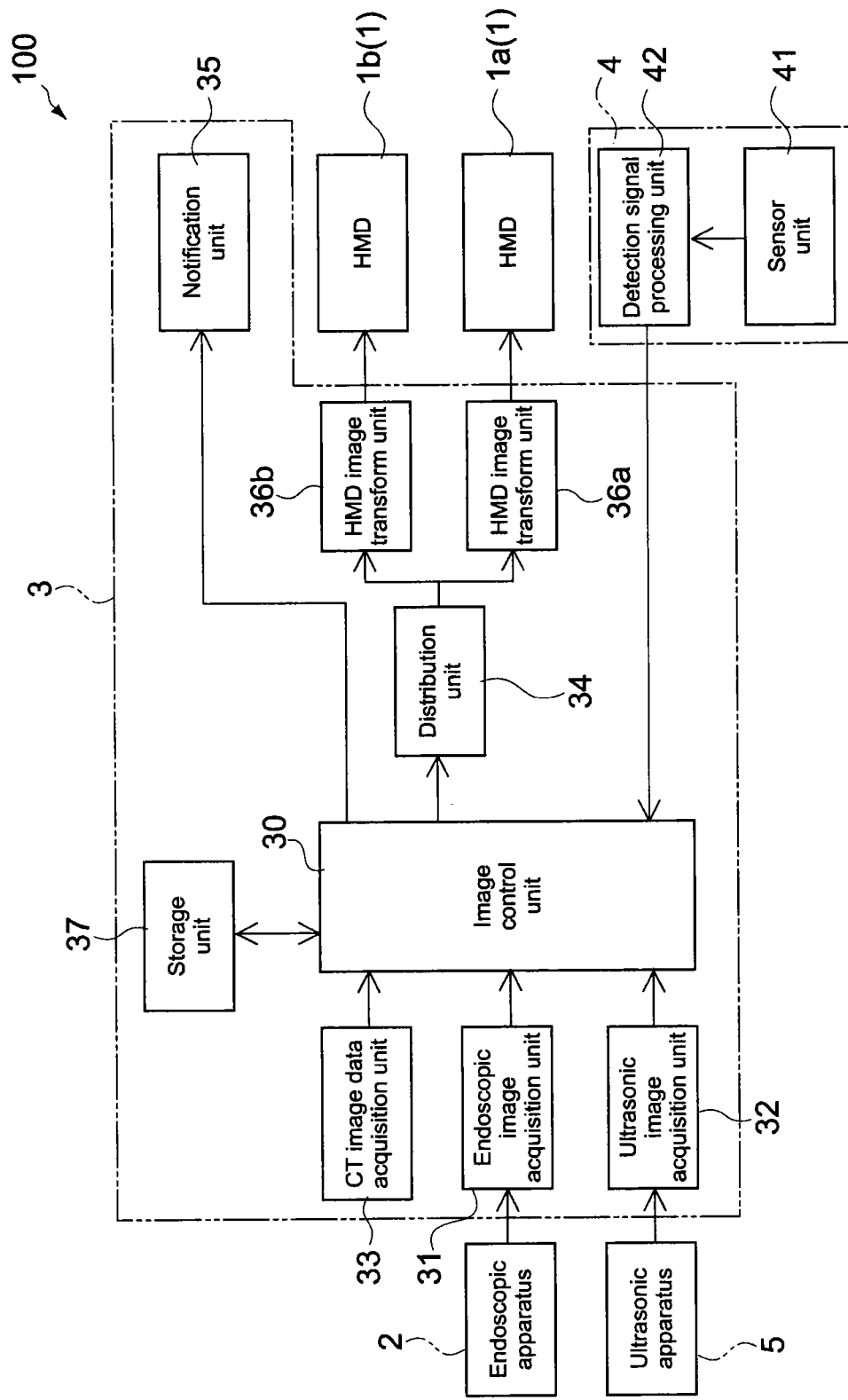
FIG. 2 A block diagram showing a configuration of the endoscopic surgery assisting system shown in FIG. 1.

FIGS. 1 and 2 are diagrams showing an endoscopic surgery assisting system according to an embodiment of the present technology. FIG. 1 is a schematic view showing a configuration of the endoscopic surgery assisting system. FIG. 2 is a block diagram showing a configuration of the endoscopic surgery assisting system. An endoscopic surgery assisting system 100 according to this embodiment includes two head-mounted displays (HMDs) 1a and 1b, an endoscopic apparatus 2, a controller 3, a detector 4, and an ultrasonic apparatus 5.

The endoscopic apparatus 2 and the ultrasonic apparatus 5 are connected to the controller 3 via cables 23 and 52, respectively. The controller 3 is also connected to the HMDs 1a and 1b via cables 15a and 15b, respectively. That is, the endoscopic surgery assisting system 100 is configured such that image data, for example, captured by the endoscopic apparatus 2 and the ultrasonic apparatus 5 is supplied to the controller 3 and an endoscopic image, an ultrasonic image, and the like are displayed on the HMDs 1a and 1b via the controller 3.

The endoscopic surgery assisting system 100 according to this embodiment is used for, for example, endoscopic surgery such as partial nephrectomy. That is, a health professional termed "endoscopist" inserts the endoscopic apparatus 2 into the body of a patient and captures an image and an operator (surgeon) performs a surgical operation such as excision on an affected area. At this time, for example, the surgeon and the endoscopist wear the HMDs 1a and 1b and can proceed with the surgical operation while checking an endoscopic image of an affected area such as a kidney which is captured by the endoscopic apparatus 2.

The HMD 1a is provided with the detector 4 capable of detecting an operation of the surgeon or the like worn by the HMD 1a. This receives, for example, control to switch endoscopic images displayed on the HMDs 1a and 1b to ultrasonic images according to a predetermined motion of the surgeon or the like wearing the HMD 1a. Thus, referring to a desired diagnosis image, a suitable surgical operation can be performed.

Note that, in the following description, a plurality of persons wearing the HMDs 1a and 1b that includes the surgeon will be referred to as a "wearer." The HMDs 1a and 1b according to this embodiment have, as will be described later, the same configurations except for the presence and absence of the detector 4. Thus, each of the HMDs 1a and 1b will be also referred to as an HMD 1.

Next, a configuration of each unit of the endoscopic surgery assisting system 100 will be described in detail.

(Endoscopic Apparatus)

The endoscopic apparatus 2 includes, for example, an insertion portion 21 and an operation portion 22. The endoscopic apparatus 2 is configured to be capable of imaging an affected area of the patient.

The insertion portion 21 has a tubular structure that can be inserted into the body. The insertion portion 21 includes, therein, an imaging element such as a CMOS image sensor (not shown) for capturing the affected area and an optical system such as a lens. Alternatively, two imaging elements, two optical systems, and the like of the endoscopic apparatus 2 may be provided for capturing right eye and left eye images having disparity, for example. With this, data of three-dimensional images for stereoscopically displaying the affected area can be obtained. The operation portion 22 is held by the wearer and configured to be capable of performing an operation or the like of the insertion portion 21.

The endoscopic image data captured by the endoscopic apparatus 2 is output to the controller 3 via a cable 23. The endoscopic image is displayed on a monitor M, which will be described later, for example, and presented also to a person not wearing the HMD 1.

Alternatively, the endoscopic apparatus 2 may include a light source (not shown). The light emitted from a light source is introduced into an end of the insertion portion 21 via, for example, a light guiding fiber or the like housed in the insertion portion 21.

(Ultrasonic Apparatus)

During surgery, the ultrasonic apparatus 5 emits a ultrasonic wave to an affected area from a probe (not shown) and receives the ultrasonic wave reflected from the affected area to produce original ultrasonic image data. Here, the "original ultrasonic image data" is image data generated by the ultrasonic apparatus 5 according to a predetermined standard and generated with a predetermined screen size and a predetermined number of pixels. The original ultrasonic image data generated by the ultrasonic apparatus 5 is output to the controller 3 via a cable 52.

Alternatively, the ultrasonic apparatus 5 may have a monitor 51 capable of displaying an original ultrasonic image (see FIG. 1). With this, the ultrasonic image can be displayed also by a person not wearing the HMD 1.

(HMD)

Figure 3:
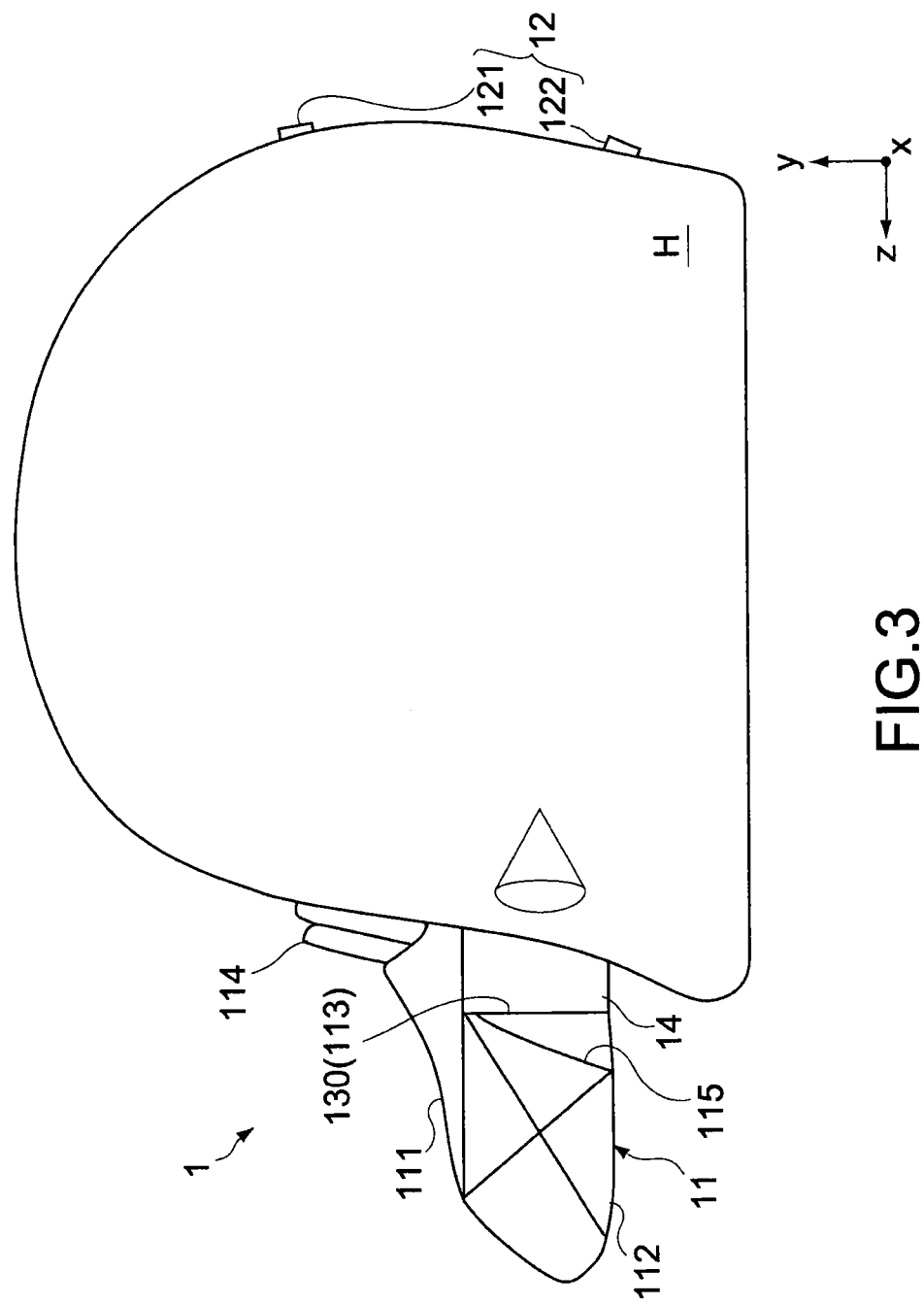
Figure 4:
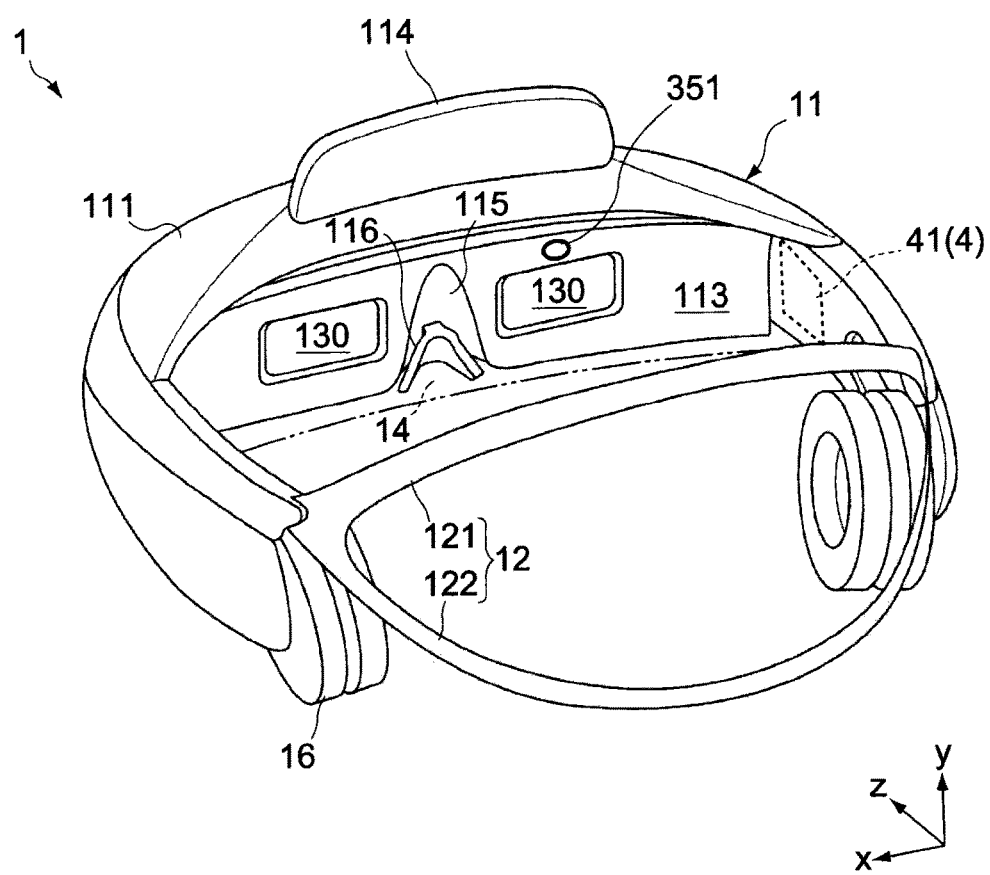
FIG. 4 A perspective view of the HMD shown in FIG. 3, as viewed facing display surfaces.
Figure 5:
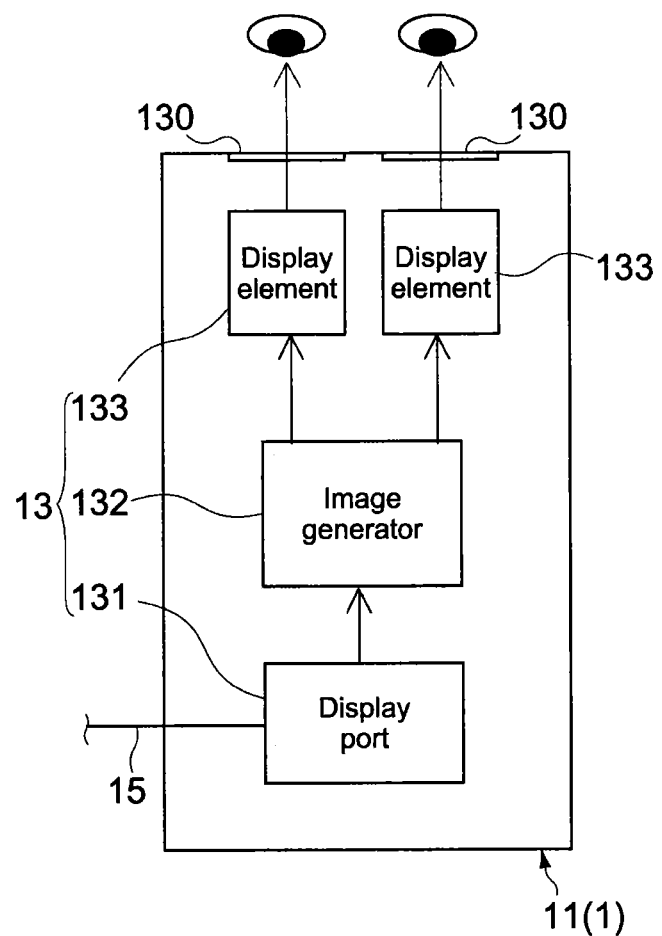
FIG. 5 A block diagram showing an internal configuration of the HMD shown in FIG. 3.

FIGS. 3 to 5 are diagrams showing a configuration of the HMD according to this embodiment. FIG. 3 is a cross-sectional view of the HMD worn by the wearer as viewed in an x-axis direction. FIG. 4 is a perspective view as viewed facing a display surface. In FIG. 3, H indicates the wearer.

Note that the x-axis direction, a y-axis direction, and a z-axis direction in the figures indicate three-axis directions mutually orthogonal in an xyz-coordinate system belonging to the HMD 1. It is assumed that the x-axis direction is left- and right-hand directions of the HMD 1. It is assumed that the y-axis direction is upper and lower directions of the HMD 1. It is assumed that the z-axis direction is front and rear directions of the HMD 1. It is also assumed that, with the HMD 1 being worn by the wearer, the x-axis direction is left- and right-hand directions of the wearer, the y-axis direction is upper and lower directions of the wearer, and the z-axis direction is front and rear (front-back) directions of the wearer.

The HMD 1 includes a casing 11, display surfaces 130 for a left eye and a right eye, an opening 14, and a display unit 13 that causes the display surfaces 130 to display images. The HMD 1 according to this embodiment is configured as, for example, a non-see through HMD generally having a goggles-like shape. Each of the HMDs 1*a* and 1*b* is connected to the controller 3 through, for example, the cables 15*a* and 15*b* (see FIG. 1). Note that the display surfaces 130 will be denoted by the same reference symbols because those for the left and right eyes have the same configurations. The cables 15*a* and 15*b* will be also referred to as cables 15.

The casing 11 can be placed before the eyes of the wearer and is configured to fit the face of the wearer. The casing 11 includes an upper surface 111 and a lower surface 112 and is as a whole formed in a semi-disk shape that is expanded in the z-axis direction, for example. On the upper surface 111, a pad portion 114 that is in contact with the forefront of the wearer to fix a mounting portion of the casing 11 during mounting may be disposed. Alternatively, a mounting portion 12 which will be described later may be connected to left and right side surfaces of the casing 11 is connected and headphones 16 may be arranged.

Further, the casing 11 includes an eyepiece surface 113. The eyepiece surface 113 is opposed to the face including the left and right eyes of the wearer at a predetermined distance in the z-axis direction. The eyepiece surface 113 is substantially orthogonal to the z-axis direction. The eyepiece surface 113 is provided continuously with the lower surface 112 at a lower end, for example. Further, a cutout 115 is formed at the center of the eyepiece surface 113 to conform with the shape of the nose of the wearer, for example. In addition, a nose pad 116 configured to be detachable, for example, may be placed in the cutout 115. Note that FIG. 3 shows the nose pad 116 detached.

Further, an LED lamp 351 to be described later is disposed on the eyepiece surface 113. The LED lamp 351 is placed in a region visible by the wearer. For example, the LED lamp 351 is placed above the display surface 130. The LED lamp 351 is configured to light on an image control mode of the controller 3 to be described later. With the LED lamp 351, it is possible to notify the wearer of the image control mode on which an image can be controlled based on an operation of the wearer of the HMD 1*a*.

The display surfaces 130 are supported by the casing 11 and present images to the wearer. That is, the display surfaces 130 are configured to present the images for the left and right eyes, which are obtained by an endoscopic image acquisition unit 31, an ultrasonic image acquisition unit 32, and the like and processed, to the left and right eyes of the wearer.

In this embodiment, the display surfaces 130 are placed in the eyepiece surface 113 of the casing 11 and arranged along the x-axis direction. The display surfaces 130 are provided substantially orthogonal to the z-axis direction such that an optical axis of emitted image light is substantially parallel to the z-axis direction, for example. The shape and size of the display surfaces 130 are not particularly limited. For example, each of the display surfaces 130 has a rectangular shape. The material for the display surfaces 130 is not particularly limited as long as it has a transmittance. For example, a plastic plate or a glass plate is employed.

The opening 14 is formed in the casing 11. The opening 14 is configured to be capable of providing a wearer such as an operator with a field of view at hand. The configuration of the opening 14 is not particularly limited. For example, the opening 14 is formed of a spacing between the lower surface 112 of the casing 11 and the face of the wearer, the spacing being formed with the eyepiece surface 113 and the face of the wearer being opposed to each other at the predetermined distance. This makes it possible for the operator to check the field of view at hand through the opening 14 when viewing below the display surfaces 130. In addition, if the nose pad 116 is configured to be detachable, the nose pad 116 is detached and the HMD 1 is mounted, such that the field of view through the opening 14 can be further widened.

The HMD 1 further includes the mounting portion 12 configured to enable the casing 11 to be mounted at a suitable relative position. The configuration of the mounting portion 12 is not particularly limited. For example, the mounting portion 12 includes an upper band 121 and a lower band 122. The upper band 121 and the lower band 122 are connected to the casing 11 and mounted on the back of the head of the wearer. For the upper band 121 and the lower band 122, a soft material such as nylon and polypropylene or a flexible material such as silicone rubber and elastomer are appropriately employed, for example. Alternatively, the upper band 121 and the lower band 122 may be integrally formed. Alternatively, they may have variable lengths.

FIG. 5 is a block diagram of the HMD 1 showing a configuration of the display unit 13. The display unit 13 includes a display port input terminal 131, an image generator 132, and display elements 133. The display unit 13 is housed in the casing 11. The display port input terminal 131 is, for example, connected to the controller 3 through the cable 15 and obtains an image control signal serving as the image data. The image generator 132 generates, based on the image control signal, an image signal to be output to each of the left and right display elements 133. The display elements 133 emit image light corresponding to these image signals to each of the display surfaces 130. In this manner, an image is presented to the wearer. Note that the display elements 133 have the same configurations for the left and right eyes as in the display surfaces 130, and hence will be denoted by the same symbols.

Specifically, the image generator 132 may perform predetermined shifting processing or the like on the above-mentioned image control signal to generate image signals for the left and right eyes that are suitable for the HMD 1. This makes it possible to present a three-dimensional image to the wearer. An shift amount in the shifting processing is calculated based on, for example, a distance between the display elements 133 of the HMD 1 and the eyes, a distance between the both eyes, or a virtual image position to be described later.

The left and right display elements 133 emit image light to the left and right display surfaces 130 based on the image signals input from the image generator 132. In this embodiment, the display elements 133 are formed of organic EL (Electroluminescence) elements. Due to the provision of the organic EL elements as the display elements 133, it is possible to achieve downsizing, high contrast, a rapid response, and the like.

The display elements 133 have such a configuration that, for example, red organic EL elements, green organic EL elements, and blue organic EL elements are arranged in a matrix form. When driven by a drive circuit of an active matrix type or a simple (passive) matrix type, each of these elements emits light by itself at its predetermined timing, luminance, and the like. The display elements 133 are configured such that a predetermined image is displayed as a whole of the display elements 133 in such a manner that the drive circuit is controlled based on the image signals generated by the image generator 132.

Note that the display elements 133 are not limited to have the above-mentioned configuration. For example, liquid-crystal display (LCD) elements may be employed.

For example, a plurality of eyepiece lenses (not shown) are provided as the optical system between the display elements 133 and the display surfaces 130. By providing these eyepiece lenses and the eyes of the wearer to be opposed to each other with a predetermined distance therebetween, it becomes possible for the wearer to observe a virtual image that appears to be displayed at a predetermined position (virtual position). The virtual position and the size of the virtual image are set depending on the configurations or the like of the display elements 133 and the optical system. For example, the size of the virtual image is 750 inches equivalent to a movie theater screen size and the virtual position is set to be about 20 m away from the wearer. For observation of the virtual image, the casing 11 is located at a suitable position relative to the wearer such that image light emitted from the display elements 133 with the z-axis direction being an optical axis direction forms an image on each of the retina of the left and right eyes via the eyepiece lenses or the like.

The HMD 1a having the above-mentioned configuration includes the detector 4. Hereinafter, the detector 4 will be described.

(Detector)

The detector 4 is worn by the wearer and configured to be capable of detecting a motion of the wearer. In this embodiment, the detector 4 is mounted on the HMD 1a.

The detector 4 includes a sensor unit 41 capable of detecting a motion of the wearer. The position of the sensor unit 41 is not particularly limited. For example, the sensor unit 41 is provided in vicinity of a surface of the casing 11 of the HMD 1a, which is in contact with the wearer (see FIG. 4).

The sensor unit 41 includes three acceleration sensors capable of detecting accelerations along the x-axis direction, the y-axis direction, and the z-axis direction and three angular velocity sensors capable of detecting angular velocities around an x-axis, a y-axis, and a z-axis. The sensor unit 41 is configured as a so-called six-axis motion sensor. The detector 4 may be, for example, configured as a package component in which the three acceleration sensors and the three angular velocity sensors are mounted on one or more circuit boards or the like.

The acceleration sensors are not particularly limited. However, for example, acceleration sensors of a piezo-resistive type, a piezoelectric type, a capacitive type, or the like can be used. Further, the angular velocity sensors are not particularly limited. However, for example, a vibration type gyro sensor, a rotary top gyro sensor, a laser ring gyro sensor, and a gas rate gyro sensor can be appropriately selected.

In this embodiment, the detector 4 further includes a detection signal processing unit 42. The detection signal processing unit 42 performs predetermined processing such as A/D (Analog/Digital) conversion and amplification on a signal output from the sensor unit 41. The detection signal processing unit 42 may be mounted on the same circuit board as the sensor unit 41. However, it is not limited thereto. For example, the detection signal processing unit 42 may be placed in vicinity of the sensor unit 41 of the HMD 1a or may be placed in the same casing as the controller 3.

The detector 4 outputs a detection signal processed by the detection signal processing unit 42 to the controller 3.

(Controller)

The controller 3 is configured to be capable of causing the HMD 1 to display an image. In this embodiment, the controller 3 includes an image control unit 30, the endoscopic image acquisition unit 31, the ultrasonic image acquisition unit 32, a CT image acquisition unit 33, a distribution unit 34, a notification unit 35, and a storage unit 37. The elements of the controller 3 are, for example, housed in a single casing.

The endoscopic image acquisition unit 31 is configured to be capable of obtaining the endoscopic image data of the affected area of the patient. In this embodiment, the endoscopic image acquisition unit 31 includes an input terminal and an image conversion circuit (not shown). The input terminal is connected to the endoscopic apparatus 2 and supplied with the endoscopic image data captured by the endoscopic apparatus 2. For example, the image conversion circuit converts the standard of the image data supplied from the endoscopic apparatus 2. Note that the image data subjected to image conversion or the like in the endoscopic image acquisition unit 31 will be also referred to as "endoscopic image data."

The endoscopic image acquisition unit 31 includes, in this embodiment, a digital zoom circuit (not shown). The digital zoom circuit is capable of generating, for example, image data in which the magnification of the endoscopic image data is changed. That is, the endoscopic image acquisition unit 31 trims the periphery of the endoscopic image data through the digital zoom circuit and enlarges pixels at the center, to thereby generate image data in which the magnification of the endoscopic data is increased. In contrast, the endoscopic image acquisition unit 31 reduces the size of pixels of the entire endoscopic image data, to thereby generate image data in which the magnification of the endoscopic data is reduced.

Note that, for example, the endoscopic image acquisition unit 31 may be also capable of generating a three-dimensional image to be output to a monitor 24 to be described later.

The ultrasonic image acquisition unit 32 is configured to be capable of obtaining ultrasonic image data of an affected area of a patient. In this embodiment, the ultrasonic image acquisition unit 32 includes an input terminal and an up-converter. The input terminal is connected to the ultrasonic apparatus 5 and supplied with the original ultrasonic image data generated by the ultrasonic apparatus 5.

The ultrasonic image acquisition unit 32 is configured to be capable of obtaining the ultrasonic image data by image-converting (up-converting) the original ultrasonic image data, for example, through the up-converter. The "ultrasonic image data" means image data of a standard compatible with the HMD 1 and is generated with a screen size and number of pixels that are different from those of the original ultrasonic image data.

In this embodiment, the number of pixels of an image compatible with the HMD 1 is larger than the number of pixels of an image generated by the ultrasonic apparatus 5. With this, when the original ultrasonic image data is displayed on the HMD 1, the pixels are extended and displayed, and hence there is a fear that a defect such as a blur of an image occurs. The aspect ratio (e.g., 16:9) of the image compatible with the HMD 1 can be different from the aspect ratio (e.g., 4:3) of the image generated by the ultrasonic apparatus 5. Thus, by performing pixel conversion, size conversion, or the like on the original ultrasonic image data, the ultrasonic image acquisition unit 32 can generate ultrasonic image data good in reproducibility of the original ultrasonic image.

The CT image acquisition unit 33 is configured to be capable of obtaining CT image data relating to an affected area. In this embodiment, the CT image acquisition unit 33 includes an input terminal and an image processing circuit (not shown). The input terminal is connected to an external memory or the like that stores original CT image data captured before the surgery. The image processing circuit generates CT image data from the original CT image data.

The CT image acquisition unit 33 uses the image processing circuit to project, for example, the obtained original CT image data in a virtual plane corresponding to a predetermined viewpoint, to thereby generate the CT image data. The "original CT image data" means three-dimensional volume data constructed based on a plurality of two-dimensional cross-sectional image data pieces obtained by CT imaging. Further, the "CT image data" means image data for stereoscopically expressing a site in a body of a patient, which is generated based on the original CT image data, and thus image data for providing a three-dimensional CT image via the HMD 1.

Alternatively, the CT image acquisition unit 33 may include a memory that stores the original CT image data and the like. Alternatively, although not shown, the CT image acquisition unit 33 may be connected to the storage unit 37 to be described later and may be configured to store the obtained CT image data and original CT image data in the storage unit 37.

The image control unit 30 is configured to be capable of controlling the endoscopic image data and the like based on an output from the detector 4. Specifically, the image control unit 30 judges, based on the output from the detector 4, whether or not a motion set in advance is performed by the wearer, and then switches output image data to the image data.

In this embodiment, the image control unit 30 judges whether or not a predetermined operation is performed combining outputs from the three acceleration sensors and the three angular velocity sensors of the detector 4. As will be described later, this makes it possible to judge various motions of the wearer such as shaking the head, looking into something, and looking upward, for example.

For example, the endoscopic image data, the ultrasonic image data, and the CT image data are employed as the image data output by the image control unit 30. Alternatively, if either the ultrasonic image data or the CT image data may be employed, it may relate to an affected area of a patient that is displayed using the endoscopic image. In addition, the image control unit 30 is capable of employing, as this image data, image data in which the magnification of the endoscopic image data generated by the endoscopic image acquisition unit 31 is changed, the CT image data in which the viewpoint is changed depending on a motion of the wearer, which is generated by the CT image acquisition unit 33, or the like.

In this embodiment, the image control unit 30 takes two modes of an image control mode and a malfunction prevention mode. On the image control mode, a judgment result relating to an image switching motion for switching the endoscopic image or the like is validated. On the malfunction prevention mode, the judgment result relating to the image switching motion is invalidated. If it is judged, based on the output from the detector 4, that a predetermined control start motion is detected, the image control unit 30 is configured to be shifted from the malfunction prevention mode to the image control mode.

For example, on the image control mode, the image control unit 30 outputs the image data based on the judgment result of the image control unit 30. On the other hand, on the malfunction prevention mode, the image control unit 30 does not output the image data based on the judgment result of the image control unit 30. That is, the image displayed on the HMD 1 is switched based on a motion of the wearer on the image control mode while the image displayed on the HMD 1 is not switched even if the wearer performs a motion on the malfunction prevention mode. With this, it is possible to prevent the image of the HMD 1 from being switched according to a motion unintentionally performed by the wearer.

The distribution unit 34 distributes image data pieces output from the image control unit 30 at substantially the same level and outputs the image data pieces to each of the HMDs 1*a* and 1*b*. This makes it possible for the controller 3 to cause each of the HMDs 1*a* and 1*b* to display the same image.

When the image control unit 30 is shifted to the image control mode, the notification unit 35 is configured to be capable of notifying the wearer of information on this. In this embodiment, the notification unit 35 includes, for example, the LED lamp 351. That is, the notification unit 35 can notify that the image control unit 30 is on the image control mode by lighting the LED lamp 351. Note that the lighting form of the LED lamp 351 is not particularly limited. For example, the LED lamp 351 may keep lighting while the image control mode is kept or may light only when the shift to the image control mode is performed.

The position of the LED lamp 351 is not particularly limited. As mentioned above, the LED lamp 351 is located above the display surface 130 in the eyepiece surface 113. With this, the LED lamp 351 can be located in a region in the field of view of the wearer who gazes the display surfaces 130. Without largely changing the eye direction, the wearer can notice the lighting LED lamp 351. Alternatively, the LED lamp 351 may be provided on only the HMD 1*a* or may be provided on both the HMDs 1*a* and 1*b*.

The controller 3 may include HMD image transform units 36*a* and 36*b* connected to the HMDs 1*a* and 1*b*, respectively. The HMD image transform units 36*a* and 36*b* are, for example, configured to be capable of transforming the image data generated by the image control unit 30 or the like into a standard compatible for the HMDs 1*a* and 1*b*.

The storage unit 37 is typically formed of a RAM (Random Access Memory), a ROM (Read Only Memory), another semiconductor memory, or the like. The storage unit 37 stores programs used for various calculations performed by the controller 3, control parameters corresponding to various operations for controlling an image, and the like. Note that the storage unit 37 may be connected to the CT image acquisition unit 33 and may be configured to be capable of storing the obtained CT image data and original CT image data and supplying the image control unit 30 with these image data pieces.

The image data output from the controller 3 is output to the HMD 1 via the cable 15 and images corresponding to this image data are displayed through the display surfaces 130 of the HMD 1 (see FIG. 1).

Note that the endoscopic surgery assisting system 100 may include the monitor M (see FIG. 1). The monitor M is, for example, connected to the controller 3 via a cable M1 and configured to be capable of displaying an image based on the image data output from the controller 3. With this, the image presented to the HMD 1 can be presented also to a person not wearing the HMD 1. The configuration of the monitor M is not limited to the above. For example, the monitor M may be connected to the endoscopic apparatus 2 and configured to be capable of displaying only the endoscopic image.

Next, an operation of the thus configured controller will be described.

[Operation of Controller]

Figure 6:
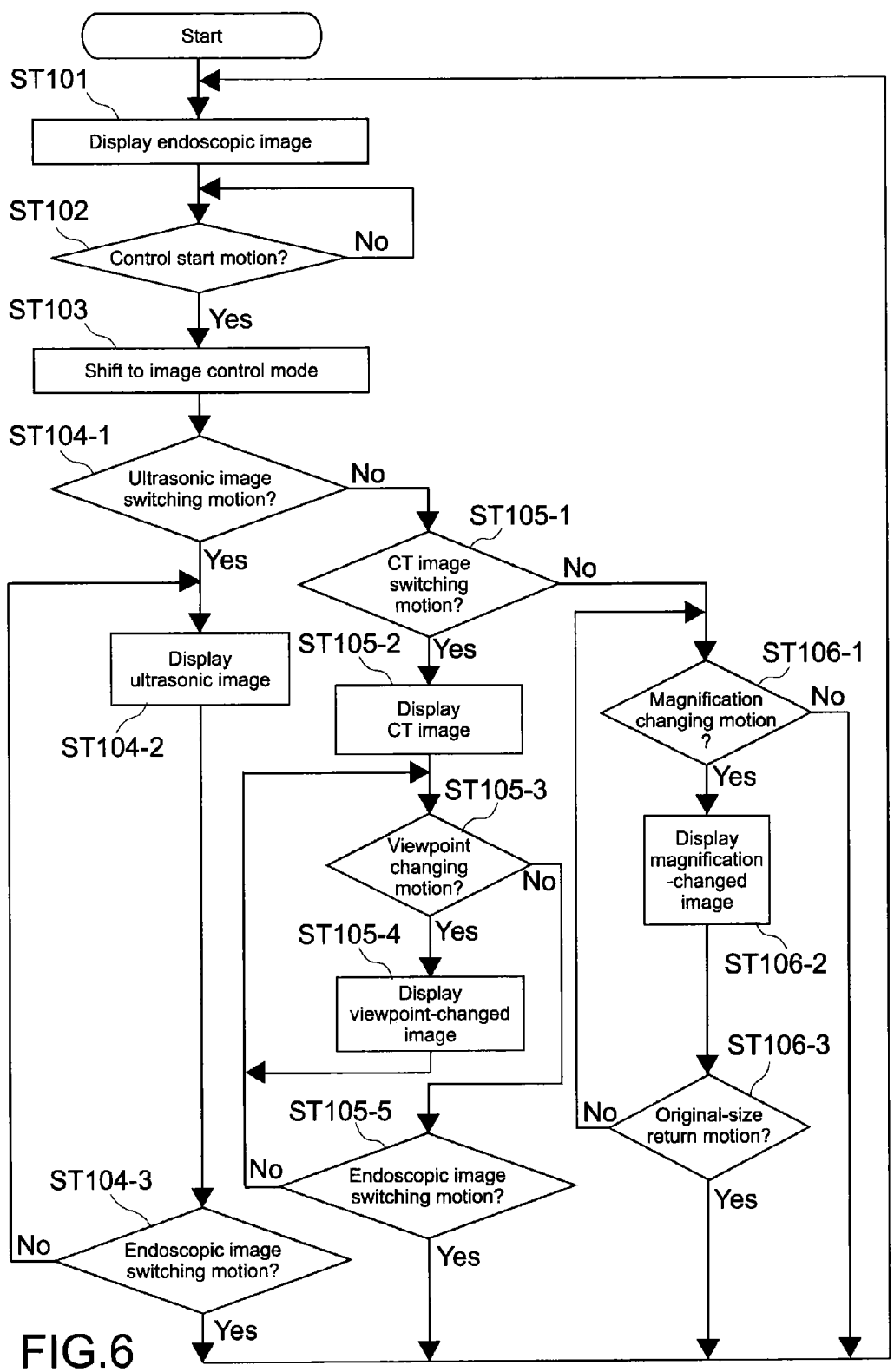
FIG. 6 A flowchart for explaining an operation of an image control unit shown in FIGS. 1 and 2.

FIG. 6 is a flowchart explaining an operation example of the controller 3. Here, the operation example when an endoscopic image is displayed on the HMD 1 and controlled based on a motion of a wearer will be described.

First, the controller 3 outputs endoscopic image data obtained by the endoscopic image acquisition unit 31 to the HMD 1 and performs control to display the endoscopic image (ST101). At this time, the image control unit 30 is on the malfunction prevention mode, on which the judgment result based on the output of the detector 4 is invalidated.

On the other hand, the image control unit 30 of the controller 3 monitors outputs of the three acceleration sensors and the three angular velocity sensors of the detector 4 and judges whether or not the control start motion is performed (ST102). For the control start motion, a motion that will rarely be performed as motions during endoscopic surgery can be employed. For example, a motion of looking upward for a certain period of time can be employed. With this, it is possible to prevent it from being erroneously shifted to the image control mode.

Specifically, the image control unit 30 is capable of detecting the looking-up motion based on an acceleration in the y-axis direction that is output from the acceleration sensor and a rotational speed around the x-axis that is output from the angular velocity sensor. In addition, when this motion is continued for a certain period of time, it is judged that the control start motion is performed.

If it is judged that the control start motion is not performed (No in ST102), the image control unit 30 continues monitoring the outputs from the detector 4 (ST102).

If it is judged by the image control unit 30 that the control start motion is performed (Yes in ST102), the image control unit 30 is shifted to the image control mode (ST103). At this time, the notification unit 35 notifies the wearer of the shift to the image control mode by lighting the LED lamp 351.

On the image control mode, the image control unit 30 judges, based on the output from the detector 4, whether or not a predetermined image switching motion is performed. In this embodiment, the image switching motion includes an ultrasonic image switching motion for switching the image data output by the image control unit 30 from the endoscopic image data to the ultrasonic image data, a CT image switching motion for switching from the endoscopic image data to the CT image data, and a magnification changing motion for changing the magnification of the endoscopic image. In this embodiment, although the specific aspects of these motions are not particularly limited, specific examples of the motions including the image switching motion and examples of the outputs of the detector 4 that are associated with the motions will be shown in Table 1 below. Hereinafter, a description will be made with reference to Table 1.

TABLE 1

| Motion | Specific example | Related output of detector |
|---|---|---|
| Ultrasonic image switching motion | Motion of shaking head successively two or more times (left) | Acceleration in x-axis direction and rotational speed around y-axis direction |
| CT image switching motion | Motion of shaking head successively two or more times (right) | Acceleration in x-axis direction and rotational speed around y-axis direction |
| Magnification changing motion | Motion of looking upward successively two or more times | Acceleration in y-axis direction and rotational speed around x-axis direction |
| Viewpoint changing motion | Motion of slowly moving head | Accelerations or the like in z-axis direction |
| Original-size return motion | Motion of resting and then looking into something | Accelerations or the like in x-, y-, and z-axis directions |

First, the image control unit 30 judges, based on the output from the detector 4, whether or not the ultrasonic image switching motion is performed (ST104-1). If it is judged that the ultrasonic image switching motion is performed (Yes in ST104-1), the image control unit 30 outputs the ultrasonic image data instead of the endoscopic image data and causes the HMD 1 to display the ultrasonic image (ST104-2). Although the ultrasonic image switching motion is not particularly limited, it may be, for example, as shown in Table 1, a motion of shaking the head to the left successively two or more times.

Specifically, the image control unit 30 judges the ultrasonic image switching motion in the following manner. That is, the image control unit 30 is capable of detecting a motion of shaking the head to the left based on an acceleration in the x-axis direction that is output from the acceleration sensor and a rotational speed around the y-axis that is output from the angular velocity sensor. The image control unit 30 can judge that the ultrasonic image switching motion is performed if detecting the motion of shaking the head to the left successively two or more times.

After the ultrasonic image is displayed on the HMD 1, the image control unit 30 judges whether or not an endoscopic image switching motion is performed (ST104-3). Although not particularly limited, the endoscopic image switching motion may be, for example, the motion of shaking the head to the left successively two or more times as in the ultrasonic image switching motion.

If it is judged that the endoscopic image switching motion is not performed by the image control unit 30 (No in ST104-3), the image control unit 30 continues outputting the ultrasonic image data (ST104-2). If it is judged that the endoscopic image switching motion is performed by the image control unit 30 (Yes in ST104-3), the image control unit 30 outputs the endoscopic image data instead of the ultrasonic image data and causes the HMD 1 to display the endoscopic image again (ST101).

Note that, when the processing returns to the step (ST101) of causing the HMD 1 to display the endoscopic image through the sequence of steps, the image control unit 30 may be configured to be automatically shifted from the image control mode to the malfunction prevention mode.

If it is judged that the ultrasonic image switching motion is not performed (No in ST104-1), the image control unit 30 judges whether or not the CT image switching motion is performed (ST105-1). If it is judged that the CT image switching motion is detected (Yes in ST105-1), the image control unit 30 outputs the CT image data instead of the endoscopic image data and causes the HMD 1 to display the CT image (ST105-2). Although not particularly limited, the CT image switching motion may be, for example, as shown in Table 1, a motion of shaking the head to the right successively two or more times.

Specifically, the image control unit 30 is capable of detecting a motion of shaking the head to the right based on the acceleration in the x-axis that is output from the acceleration sensor and the rotational speed around the y-axis that is output from the angular velocity sensor. The image control unit 30 can judge that the CT image switching motion is performed if detecting the motion of shaking the head to the right successively two or more times.

After the CT image is displayed on the HMD 1, the image control unit 30 judges whether or not the viewpoint changing motion is performed (ST105-3). If it is judged that the viewpoint changing motion is performed (Yes in ST105-3), the image control unit 30 generates CT image data in which the viewpoint is changed depending on this motion and causes the HMD 1 to display (ST105-4). Although this motion is not particularly limited, it can be, for example, as shown in Table 1, a motion of slowly moving the head.

Specifically, the image control unit 30 detects an amount of movement of the head in each direction or the posture of the head based on the accelerations in the x-axis direction, the y-axis direction, and the z-axis direction that are output from the acceleration sensors and rotational speeds around the x-axis, around the y-axis, and around the z-axis direction that are output from the angular velocity sensors. The image control unit 30 is capable of generating the image data changed in angle of the viewpoint of the CT image according to the detected amount of movement in each direction.

If it is judged that a line-of-sight changing motion is not performed by the image control unit 30 (No in ST105-3), the image control unit 30 further judges whether or not the endoscopic image switching motion is performed (ST105-5). Although the endoscopic image switching motion is not particularly limited, for example, as in the CT image switching motion, it may be a motion of shaking the head to the right two times. If it is judged that the endoscopic image switching motion is not performed by the image control unit 30 (No in ST105-5), the image control unit 30 judges whether or not the viewpoint changing motion is performed again (ST105-3). If it is judged that the endoscopic image switching motion is performed by the image control unit 30 (Yes in ST105-5), the image control unit 30 outputs the endoscopic image data instead of the CT image data and causes the HMD 1 to display the endoscopic image again (ST101).

If it is judged that the CT image switching motion is not performed (No in ST105-1), the image control unit 30 judges whether or not the magnification changing motion is performed (ST106-1). If it is judged that the magnification changing motion is not performed (No in ST106-1), the image control unit 30 continuously outputs the endoscopic image data and causes the HMD 1 to display the endoscopic image (ST101).

If it is judged that the magnification changing motion is performed (Yes in ST106-1), the image control unit 30 outputs the image data in which the magnification of the endoscopic image is changed and causes the HMD 1 to display this image (ST106-2). Although the magnification changing motion is not particularly limited, it can be, for example, as shown in Table 1, a motion of resting and then looking into something.

Specifically, the image control unit 30 judges the magnification changing motion in the following manner. That is, the image control unit 30 is capable of detecting a motion of looking into something based on the amount of movement based on the acceleration in the z-axis direction that is output from the acceleration sensor and the posture of the head that is determined in view of the outputs of the angular velocity sensors. The image control unit 30 can judge that the magnification changing motion is performed if further detecting resting for a predetermined period of time (e.g., few seconds) before the motion of looking into something. The image control unit 30 generates and outputs image data in which the magnification of the endoscopic image is changed according to the detected amount of movement or the like in the z-axis direction.

After a magnification-changed image is displayed on the HMD 1, the image control unit 30 judges whether or not an original-size return motion is performed (ST106-3). Although the original-size return motion is not particularly limited, for example, a motion of looking upward successively two or more times.

Specifically, the image control unit 30 judges the original-size return motion in the following manner. That is, the image control unit 30 is capable of detecting a motion of looking upward based on the acceleration in the y-axis direction that is output from the acceleration sensor and the rotational speed around the x-axis that is output from the angular velocity sensor. The image control unit 30 can judge that the original-size return motion is performed by further detecting these motions successively two or more times. If it is judged that the original-size return motion is performed by the image control unit 30 (Yes in ST106-3), the image control unit 30 outputs the endoscopic image data whose size is returned to the original size and causes the HMD 1 to display this endoscopic image (ST101).

If it is judged that the original-size return motion is not performed (No in ST106-3), the image control unit 30 judges whether or not the magnification changing motion is performed again (ST106-1).

As described above, in accordance with this embodiment, it is possible to cause the HMD 1 to display an image according to a motion of the wearer. With this, it becomes possible to cause the HMD 1 to display the endoscopic image and other diagnosis images consulted during endoscopic surgery. Thus, it is possible to check a necessary image without the wearer moving the line of sight and to reduce fatigue during surgery.

In this embodiment, in addition to the endoscopic image, an ultrasonic image and a CT image before the surgery are employed as diagnosis images that can be displayed on the HMD 1. By consulting these images during surgery, it becomes possible to accurately grasp the condition of the affected area, distribution of veins, and the like and perform the surgical operation.

According to this embodiment, enlarging and reducing an endoscopic image and changing a viewpoint of a CT image during surgery can be performed according to motions of the operator. With this, it becomes possible to more accurately grasp the condition of the affected area and perform a precise and speedy surgical operation.

Further, the detector 4 can control the image according to the operation of the wearer. With this, even if the wearer cannot directly touch the HMD 1 and the like for sanitary reasons, it is possible to control the image according to the wearer's own intention.

Further, the image control unit 30 can be shifted between the image control mode and the malfunction prevention mode. With this, it is possible to prevent a malfunction and perform image control according to the wearer's own intention. In addition, the image switching motion can be suitably set. With this, for example, it is possible to employ a motion that will rarely be performed as motions during surgery can be employed, for example, a motion of shaking the head "successively two or more times" or a motion of "slowly" moving the head. Thus, it is possible to more surely prevent the malfunction.

Further, in this embodiment, the detector 4 is mounted on only one (HMD 1*a*) of the HMDs 1. With this, two wearers can check the same image, share information, and proceed with the surgical operation. Further, in accordance with this embodiment, the HMD 1 includes the controller 3 as a separate configuration and is capable of switching or the like of images displayed on the HMD 1. With this, outputting to the plurality of HMDs 1 becomes possible.

Further, the HMD 1 according to this embodiment includes the opening 14 that provides the wearer with a field of view at hand. With this, even if the wearer carries out the surgical operation by the use of the endoscopic apparatus 2, another surgical tool, and the like, the wearer can take a look at hand through the opening 14 and more smoothly proceed with the surgical operation.

<Second Embodiment>

Figure 7:
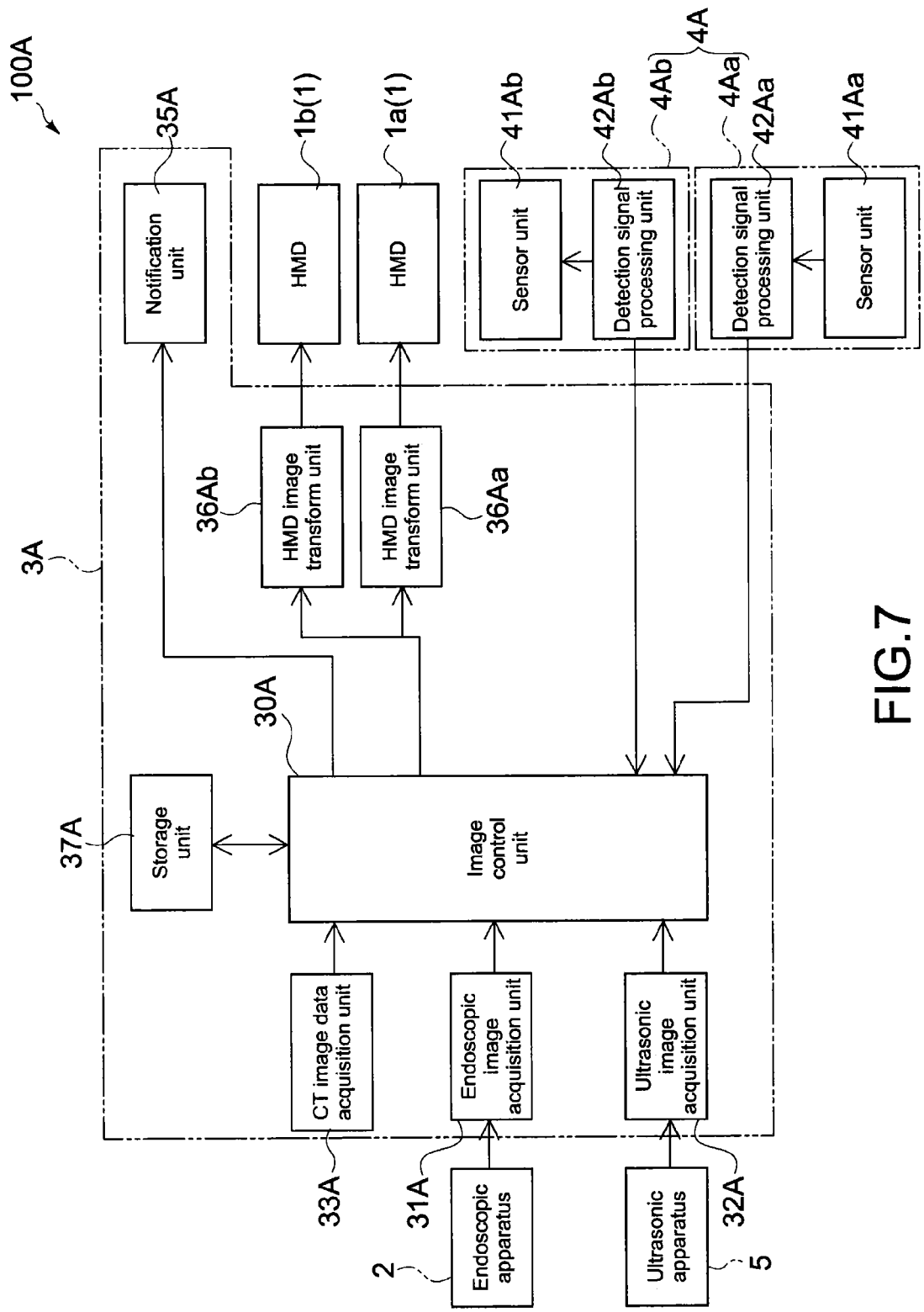
FIG. 7 A block diagram showing a configuration of an endoscopic surgery assisting system according to a second embodiment of the present technology.

FIG. 7 is a block diagram showing a configuration of an endoscopic surgery assisting system according to a second embodiment of the present technology. In an endoscopic surgery assisting system 100A according to this embodiment, a main point different from the endoscopic surgery assisting system 100 according to the first embodiment is that a detector 4A includes two detectors 4Aa and 4Ab mounted on HMDs 1*a* and 1*b*, respectively, and can control an image according to each motion of the wearer.

The HMDs 1*a* and 1*b*, the endoscopic apparatus 2, and the ultrasonic apparatus 5 are configured to be substantially identical to those of the first embodiment. That is, the HMDs 1*a* and 1*b* are worn by a plurality of persons (wearers) including an operator. The endoscopic apparatus 2 is configured to be capable of capturing an affected area of a patient and the ultrasonic apparatus 5 is configured to be capable of generating original ultrasonic image data. These configurations will be denoted by the same symbols as those of the first embodiment and detailed descriptions thereof will be omitted.

The detector 4A includes the plurality of detectors 4Aa and 4Ab. The detector 4A is worn by each of the wearers of the HMDs 1 and configured to be capable of detecting a motion of the wearer. That is, the detector 4A includes the detector 4Aa mounted on the HMD 1*a* and the detector 4Ab mounted on an HMD 1*b*.

As in the first embodiment, the detectors 4Aa and 4Ab include sensor units 41Aa and 41Ab and detection signal processing units 42Aa and 42Ab. Detection signals processed by the detection signal processing units 42Aa and 42Ab are output to the controller 3A.

The controller 3A includes an endoscopic image acquisition unit 31A, an ultrasonic image acquisition unit 32A, a CT image acquisition unit 33A, an image control unit 30A, a notification unit 35A, HMD image transform units 36Aa and 36Ab, and a storage unit 37A. Images are individually displayed on the HMDs 1*a* and 1*b* based on outputs from the image control unit 30. That is, the controller 3A is different from the controller 3 according to the first embodiment in that the controller 3A includes the image control unit 30A connected to each of the detectors 4Aa and 4Ab and does not include the division unit.

The image control unit 30A detects each motion based on outputs from the detectors 4Aa and 4Ab. That is, the image control unit 30A judges, based on the output from the detector 4Aa, whether or not a predetermined motion of the wearer of the HMD 1*a* is detected. Further, the image control unit 30A judges, based on the output from the detector 4Ab, whether or not a predetermined motion of the wearer of the HMD 1*b* is detected.

The image control unit 30A outputs image data based on the motions judged based on the outputs of the detectors 4Aa and 4Ab to the HMD image transform units 36Aa and 36Ab, respectively. With this, the image based on the motion of the wearer of the HMD 1*a* is displayed on the HMD 1*a* and the image based on the motion of the wearer of the HMD 1*b* is displayed on the HMD 1*b*.

In accordance with this embodiment, in addition to the actions and effects as those of the first embodiment, the wearers of the HMDs 1*a* and 1*b* can control the display images of the HMDs 1*a* and 1*b* according to motions of the wearers, respectively. With this, sharing of the works becomes possible and a highly efficient surgical operation can be achieved.

<Third Embodiment>

Figure 8:
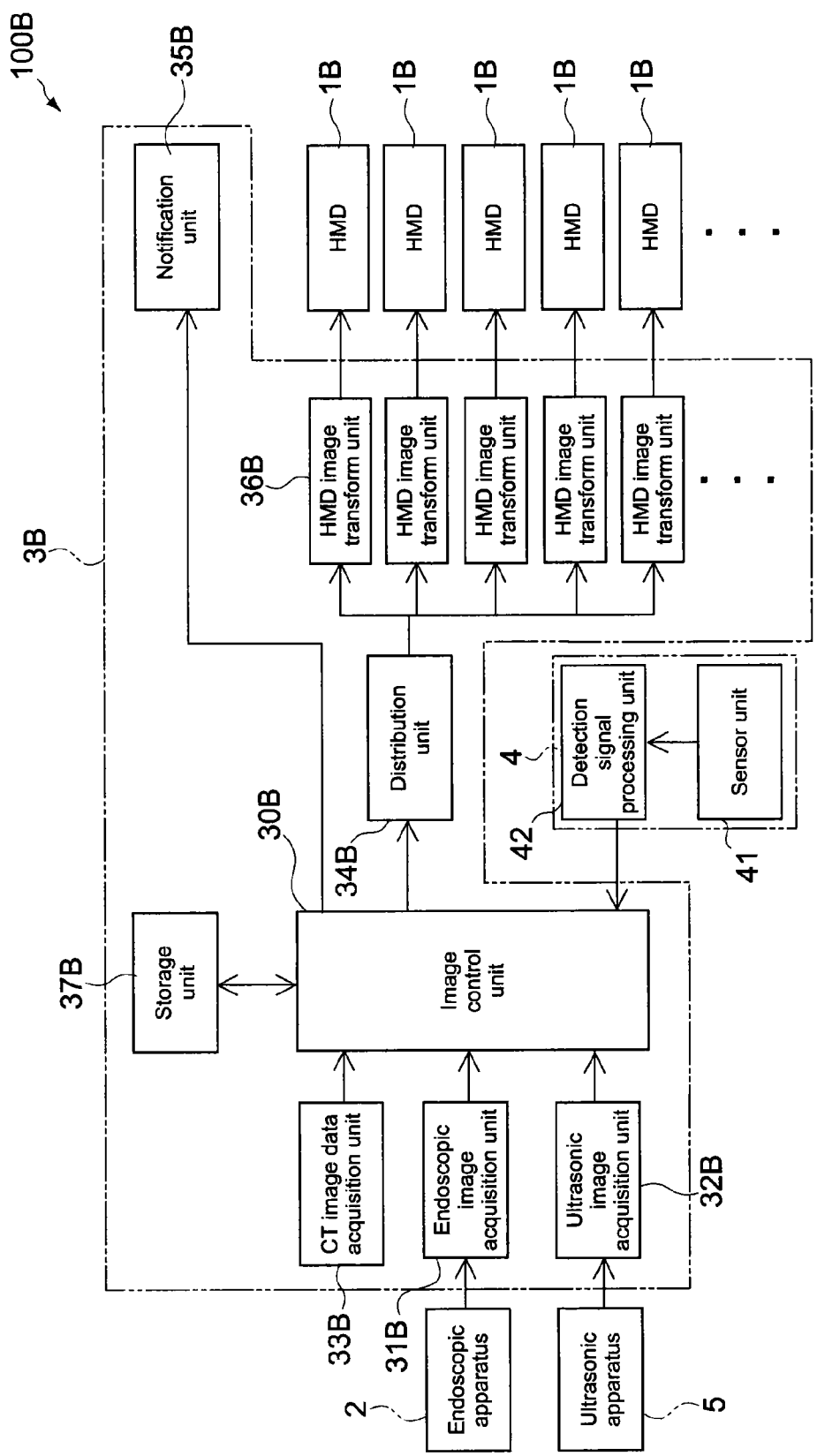
FIG. 8 A block diagram showing a configuration of an endoscopic surgery assisting system according to a third embodiment of the present technology.

FIG. 8 is a block diagram showing a configuration of an endoscopic surgery assisting system according to a third embodiment of the present technology. An endoscopic surgery assisting system 100B according to this embodiment is different from the endoscopic surgery assisting system 100 according to the first embodiment in that the endoscopic surgery assisting system 100B includes three or more HMDs 1B and a controller 3B includes a plurality of HMD image transform units 36B corresponding to the HMDs 1B. Note that other points are substantially the same as those of the first embodiment and will be therefore denoted by the same symbols as those of the first embodiment and detailed descriptions thereof will be omitted.

The plurality of HMDs 1B are, for example, worn by all the persons involved with the endoscopic surgery. The number of HMDs 1B is not particularly limited and can be appropriately set depending on the number of persons involved with the endoscopic surgery, the situation of the surgery, and the like.

The detector 4 has a configuration substantially identical to that of the detector 4 according to the first embodiment. In this embodiment, the detector 4 is mounted on one HMD 1B of the plurality of HMDs 1B. With this, the same image is displayed on all the HMDs 1B according to a motion of one of the plurality of persons (wearers) worn by the HMDs 1B.

Alternatively, the controller 3B may include the plurality of HMD image transform units 36B corresponding to the plurality of HMDs 1B. Further, a distribution unit 34B is capable of distributing the image data output from an image control unit 30B substantially at the same level and outputting to each of HMD image transform units 36B. With this, the image data selected by the image control unit 30B can be simultaneously output to the plurality of HMDs 1B based on a motion of the wearer wearing the detector 4. Note that the distribution unit 34B may include a preamplifier or the like that compensates for attenuation of signals if necessary.

In accordance with this embodiment, in addition to the actions and effects as those of the first embodiment, it is possible to proceed with the surgical operation while all persons wearing the HMDs 1B are checking the same image. Thus, it is possible to promote sharing of information, further enhance safety, and achieve a highly efficient surgical operation.

Further, in accordance with this embodiment, the controller 3B is provided as a configuration separate from the HMDs 1B and is, for example, capable of switching all images displayed on the plurality of HMDs 1B. This makes it possible to achieve multiple output of the image data. It is possible to increase the degree of freedom in the number of HMDs 1B. An endoscopic surgery assisting system with a high degree of freedom that can handle various situations can be provided.

<Fourth Embodiment>

Figure 9:
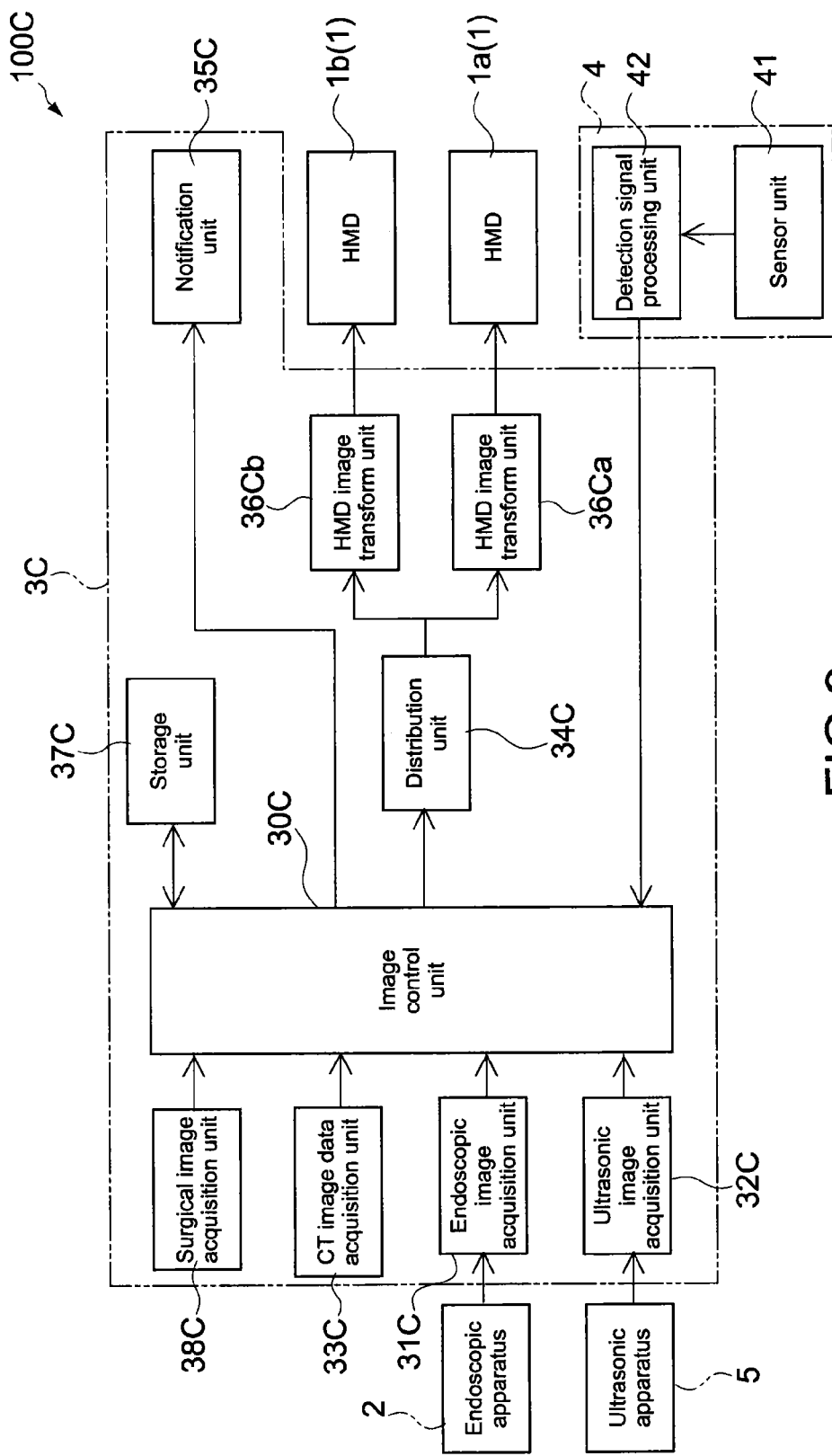
FIG. 9 A block diagram showing a configuration of an endoscopic surgery assisting system according to a fourth embodiment of the present technology.

FIG. 9 is a block diagram showing a configuration of an endoscopic surgery assisting system according to a fourth embodiment of the present technology. In an endoscopic surgery assisting system 100C according to this embodiment, a main point different from the endoscopic surgery assisting system 100 according to the first embodiment is that a controller 3C includes a surgical image acquisition unit 38C that is capable of obtaining endoscopic image data (hereinafter, referred to as surgical image data) captured by the endoscopic apparatus 2 during endoscopic surgery performed in the past. Note that other points are substantially the same as those of the first embodiment and will be therefore denoted by the same symbols as those of the first embodiment and detailed descriptions thereof will be omitted.

In this embodiment, the surgical image acquisition unit 38C includes an input terminal connected to an external memory or the like that stores the surgical image data and an image conversion circuit (not shown) that converts the standard of the surgical image data. In addition, the surgical image acquisition unit 38C may include a memory that stores the surgical image data or the like. Although not shown in the figure, the surgical image acquisition unit 38C may be connected to a storage unit 37C as will be described later or may be configured to store the surgical image data or the like in the storage unit 37.

As in the first embodiment, an image control unit 30C judges, based on the output from the detector 4, whether or not the predetermined image switching motion of the wearer is detected. The image switching motion according to this embodiment further includes a surgical image switching motion in addition to the ultrasonic image switching motion, the CT image switching motion, and the magnification changing motion the same as those of the first embodiment. Although the surgical image switching motion is not particularly limited, it may be, for example, a motion of shaking the head alternately to the left and right.

As in the first embodiment, the image control unit 30C is capable of outputting image data corresponding to the image switching motion judged according to outputs of a detector 4C and switching images displayed on the HMDs 1. As the image data, surgical image data obtained by the surgical image acquisition unit 38C is further employed in addition to the endoscopic image data, the ultrasonic image data, and the CT image data as in the first embodiment.

In accordance with this embodiment, endoscopic images of the past and the like can be displayed on the HMDs 1 based on an motion of the wearer during endoscopic surgery. With this, even if endoscopic surgery is carried out for the same patient after the first endoscopic surgery, it is possible to proceed with a surgical operation more smoothly and efficiently.

Although the embodiments of the present technology have been described above, the present technology is not limited thereto and various modifications can be made based on a technical conception of the present technology.

For example, in the above-mentioned embodiments, the detector is mounted on the HMD. However, the detector is not limited thereto as long as it is worn by the wearer including the operator. For example, the detector may be mounted on a head mounted tool different from the HMD. This also makes it possible for the detector to detect the motion of the wearer.

In the above-mentioned embodiments, the endoscopic surgery assisting system includes the endoscopic apparatus and the ultrasonic apparatus. However, the endoscopic surgery assisting system is not limited thereto. For example, the endoscopic surgery assisting system may be configured not to include these apparatuses. The endoscopic image acquisition unit and the ultrasonic image acquisition unit may obtain the endoscopic image data, the original ultrasonic image data, and the like stored in the external memory or the like and use them in order for the image control unit to control images. Alternatively, a configuration in which the endoscopic image acquisition unit includes the endoscopic apparatus and the ultrasonic image acquisition unit includes the ultrasonic apparatus may be adopted.

In the above-mentioned embodiments, the image is controlled by the detector detecting the motion of the wearer. In addition to this, for example, it may be possible to control an image according to an input operation through a foot switch or a hand switch or by audio recognition, or the like. This makes it possible to control the image even in a situation where it is difficult to move the head.

In the above, the image switching unit takes the image control mode and the malfunction prevention mode. However, it is not limited thereto and the image switching unit may be configured not to take the malfunction prevention mode. In this case, it becomes possible to control the image according to a motion of the wearer without the control start motion.

In the above-mentioned embodiments, the example in which the image control unit judges whether or not any of the ultrasonic image switching motion, the CT image switching motion, and the magnification changing motion is performed among the image switching motions in the stated order has been described. However, it is not limited thereto. The image switching motion may be judged at the same time.

In the above-mentioned embodiments, the CT image switching motion is detected after detecting the ultrasonic image switching motion. Of course, it is not limited thereto. For example, the CT image switching motion may be detected before detecting the ultrasonic image switching motion. Alternatively, switching between the ultrasonic image and the CT image may be possible.

In the above-mentioned embodiments, when the image control unit is on the malfunction prevention mode, the image switching unit does not output the image data. For example, on the malfunction prevention mode, it is also possible to make a setting such that the image control unit does not perform a judgment as to the image switching motion. Alternatively, on the malfunction prevention mode, the HMD image transform units may also be set not to output the image data to the HMDs.

In the above description, based on the viewpoint changing motion, the image in which the viewpoint of the CT image displayed on the HMD is changed is displayed. However, it is not limited thereto. For example, instead of the CT image, it may be an image in which a viewpoint of an endoscopic image, an ultrasonic image, a surgical image, or the like displayed on the HMD is changed.

In the above description, based on the magnification changing motion, an image in which the viewpoint of the endoscopic image displayed on the HMD is changed is displayed. However, it is not limited thereto. For example, instead of the endoscopic image, it may be an image in which a viewpoint of a ultrasonic image, a CT image, a surgical image, or the like displayed on the HMD is changed.

In the above description, the sensor unit of the detector is a so-called six-axis motion sensor. However, it is not limited thereto. For example, it may be configured as a so-called four-axis motion sensor including two acceleration sensors that are capable of detecting the accelerations along the x-axis direction and the y-axis direction and two angular velocity sensors that are capable of detecting the angular velocities around the x-axis and the y-axis.

In the above-mentioned embodiments, the endoscopic surgery assisting system includes the ultrasonic image acquisition unit and the CT image acquisition unit. However, the endoscopic surgery assisting system may be configured not to include one or both of them. Alternatively, the endoscopic surgery assisting system may include another image diagnosis apparatus or the like connected to the image control unit. That is, according to the present technology, it may include an image control unit as a configuration separate from the HMD and is, for example, capable of switching all images displayed on the HMDs. It is possible to increase the degree of freedom in image data to be input. An endoscopic surgery assisting system that can handle various situations can be provided.

In the second embodiment, the controller 3A may be configured to include two image control units corresponding to the detectors 4Aa and 4Ab. Also with this, it becomes possible for the controller 3A to individually display images on the HMDs 1a and 1b based on outputs from the image control units.

In the fourth embodiment, the surgical image acquisition unit 38C may be configured to be capable of obtaining not only the above-mentioned surgical image data but also other image data associated with the endoscopic surgery. With this, various images can be output according to motions of the wearer, and hence it is possible to provide the endoscopic surgery assisting system with a high degree of freedom.

Note that the present technology may also take the following configurations.
(1) An endoscopic surgery assisting system, including:
  a head-mounted display that is worn by an operator;
  a detector that is capable of detecting an motion of the operator; and
  a controller that causes the head-mounted display to display an image, the controller including an endoscopic image acquisition unit that is capable of obtaining endoscopic image data of an affected area of a patient and an image control unit that is capable of controlling the endoscopic image data based on an output from the detector and performing control to display the image based on an output from the image control unit.
(2) The endoscopic surgery assisting system according to (1), in which
  the detector is mounted on the head-mounted display.
(3) The endoscopic surgery assisting system according to (1) or (2), in which
  the head-mounted display includes a plurality of head-mounted displays that are worn by a plurality of persons including the operator, and
  the controller causes the plurality of head-mounted displays to display images based on the output from the image control unit.
(4) The endoscopic surgery assisting system according to any one of (1) to (3), in which
  the image control unit judges, based on the output from the detector, whether or not an image switching motion is performed by the operator and switches, if it is judged that the image switching motion is performed, output image data to image data corresponding to the image switching motion.
(5) The endoscopic surgery assisting system according to (4), in which
  the image control unit judges, based on the output from the detector, whether or not a control start motion is performed by the operator and validates a judgment result relating to the image switching motion if it is judged that the control start motion is performed.
(6) The endoscopic surgery assisting system according to (5), further including
  a notification unit that notifies, if the image control unit validates the judgment result relating to the image switching motion, a wearer of the validation of the judgment result.
(7) The endoscopic surgery assisting system according to any one of (4) to (6), in which
  the image data corresponding to the image switching motion is either ultrasonic image data or CT image data associated with the endoscopic image data. (8) The endoscopic surgery assisting system according to any one of (4) to (6), in which
  the image data corresponding to the image switching motion is image data in which a viewpoint of the image that the controller causes the head-mounted display to display based on the output from the detector is changed.
(9) The endoscopic surgery assisting system according to any one of (4) to (8), in which
  the image data corresponding to the image switching motion is image data in which a magnification of the image that the controller causes the head-mounted display to display based on the output from the detector is changed.
(10) The endoscopic surgery assisting system according to any one of (1) to (9), in which
  the head-mounted display includes
    a casing that can be placed in front of an eye of the operator,
    a display surface that is supported by the casing and presents the image to the operator, and
    an opening that is formed in the casing and provides the operator with a field of view at hand.
(11) An endoscopic surgery assisting system, including:
  a plurality of head-mounted displays that are worn by a plurality of persons including an operator;
  a plurality of detectors that are worn by the plurality of persons and capable of detecting motions of the plurality of persons; and
  a controller that causes each of the plurality of head-mounted displays to individually display an image, the controller including an endoscopic image acquisition unit that is capable of obtaining endoscopic image data of an affected area of a patient and an image control unit that is capable of controlling each piece of the endoscopic image data based on an output from each of the plurality of detectors and performing control to display the image based on an output from the image control unit.

(12) An image control method, including:
monitoring an output from a detector that is capable of detecting a motion of an operator wearing a head-mounted display;
judging, based on the output from the detector, whether or not an image switching motion is performed by the operator; and
switching, if it is judged that the image switching motion is performed, endoscopic image data output to the head-mounted display to image data corresponding to the image switching motion.
(13) The image control method according to (12), further including:
judging, based on the output from the detector, whether or not a control start motion is performed by the operator before judging whether or not the image switching motion is performed; and
validating a judgment result relating to the image switching motion if it is judged that the control start motion is performed.
(14) The image control method according to (12) or (13), further including
judging, based on the output from the detector, whether or not an ultrasonic image switching motion is performed by the operator, in which
the step of switching the endoscopic image data includes switching, if it is judged that the ultrasonic image switching motion is performed, the endoscopic image data output to the head-mounted display to ultrasonic image data.
(15) The image control method according to any one of (12) to (14), further including:
judging, based on the output from the detector, whether or not a CT image switching motion is performed by the operator, in which
the step of switching the endoscopic image data includes switching, if it is judged that the CT image switching motion is performed, the endoscopic image data output to the head-mounted display to CT image data.
(16) The image control method according to (15), further including:
judging, based on the output from the detector, whether or not a viewpoint changing motion is performed by the operator; and
switching, if it is judged that the viewpoint changing motion is performed, image data output to the head-mounted display to image data in which a viewpoint of the image data output to the head-mounted display is changed, based on the viewpoint changing motion.
(17) The image control method according to any one of (12) to (16), further including:
judging, based on the output from the detector, whether or not a magnification changing motion is performed by the operator; and
switching, if it is judged that the magnification changing motion is performed, image data output to the head-mounted display to image data in which a magnification of the image data output to the head-mounted display is changed based on the magnification changing motion.

DESCRIPTION OF SYMBOLS 1, 1a, 1b, 1B HMD (head-mounted display)
3, 3A, 3B, 3C controller
4, 4A, 4Aa, 4Ab detector
11 casing
130 display surface
14 opening
30, 30A, 30B, 30C image control unit
31, 31A, 31B, 31C endoscopic image acquisition unit
32, 32A, 32B, 32C ultrasonic image acquisition unit
33, 33A, 33B, 33C CT image acquisition unit
100, 100A, 100B, 100C endoscopic surgery assisting system

The invention claimed is:

1. An endoscopic surgery assisting system, comprising:
a plurality of head-mounted displays that are worn by a plurality of persons including an operator;
a detector circuit coupled to a head-mounted display worn by the operator and configured to detect a motion of the operator; and
circuitry coupled to the plurality of head-mounted displays and the detector circuit and configured to
cause the plurality of head-mounted displays to display an image,
obtain endoscopic image data of an affected area of a patient,
in first mode,
control the endoscopic image data based on the motion of the operator detected by the detector circuit, and
cause the plurality of head-mounted displays to display the endoscopic image data based on the control of the endoscopic image data, and
in a second mode, ignore a predetermined motion of the operator detected by the detector circuit,
wherein the circuitry is further configured to provide an indication of a functioning mode of the system as the first mode or the second mode in at least the head-mounted display worn by the operator, the indication being separate from the image displayed.

2. The endoscopic surgery assisting system according to claim 1, wherein the detector circuit is mounted on the head-mounted display worn by the operator.

3. The endoscopic surgery assisting system according to claim 1, wherein the circuitry is further configured to
judge, based on the output from the detector circuit, whether or not an image switching motion is performed by the operator, and
switch, if it is judged that the image switching motion is performed, output image data to image data corresponding to the image switching motion.

4. The endoscopic surgery assisting system according to claim 3, wherein the circuitry is further configured to judge, based on the output from the detector circuit, whether or not a control start motion is performed by the operator and to validate a judgment result relating to the image switching motion if it is judged that the control start motion is performed.

5. The endoscopic surgery assisting system according to claim 4, wherein the circuitry is further configured to notify, upon validation of the judgment result relating to the image switching motion, a wearer that the judgment result is validated.

6. The endoscopic surgery assisting system according to claim 3, wherein the image data corresponding to the image switching motion is at least ultrasonic image data or computer tomography (CT) image data associated with the endoscopic image data.

7. The endoscopic surgery assisting system according to claim 3, wherein the image data corresponding to the image switching motion is image data in which a viewpoint of the image is changed based on the output from the detector circuit, the image data being displayed by the head-mounted display.

8. The endoscopic surgery assisting system according to claim 3, wherein the image data corresponding to the image switching motion is image data in which a magnification of the image is changed based on the output from the detector circuit, the image data being displayed by the head-mounted display.

9. The endoscopic surgery assisting system according to claim 1, wherein each of the plurality of head-mounted displays include
a casing configured to be placed in front of an eye of a corresponding wearer,
a display surface configured to be by the casing and to present the image to the corresponding wearer, and
an opening formed in the casing and configured to provide the corresponding wearer with a field of view at hand.

10. The endoscopic surgery assisting system according to claim 1, wherein the first mode is an image control mode and the second mode is a malfunction preventing mode.

11. The endoscopic surgery assisting system according to claim 1, wherein the indication is provided via a light emitting diode (LED) lamp disposed within the head-mounted display.

12. An endoscopic surgery assisting system, comprising:
a plurality of head-mounted displays that are worn by a plurality of persons including an operator;
a plurality of detector circuits that are worn by the plurality of persons and that are configured to detect motions of the plurality of persons; and
circuitry coupled to the plurality of head-mounted displays and the plurality of detector circuit and configured to
cause each of the plurality of head-mounted displays to individually display an image,
obtain endoscopic image data of an affected area of a patient,
in a first mode,
control each piece of the endoscopic image data based the motions detected by the plurality of detector circuits and performing control, and
cause the plurality of head-mounted displays to display the image based on the control of each piece of the endoscopic image data, and
in a second mode, ignore a predetermined motion of the operator detected by the detector circuit,
wherein the circuitry is further configured to provide an indication of a functioning mode of the system as the first mode or the second mode in at least the head-mounted display worn by the operator, the indication being separate from the image displayed.

13. An image control method, comprising:
monitoring, with circuitry, an output from a detector circuit that is configured to detect a motion of an operator wearing a head-mounted display;
judging, based on the output from the detector circuitry, whether or not an image switching motion is performed by the operator;
in a first mode, switching, with the circuitry and if it is judged that the image switching motion is performed, endoscopic image data output to a plurality of head-mounted displays to image data corresponding to the image switching motion, the plurality of head-mounted displays including the head-mounted display worn by the operator; and
in a second mode, ignore a predetermined motion of the operator detected by the detector circuit; and
providing an indication of a functioning mode of the system as the first mode or the second mode in at least the head-mounted display worn by the operator, the indication being separate from the image displayed.

14. The image control method according to claim 13, further comprising:
prior to the judgement of the image switching motion, judging, with the circuitry and based on the output from the detector circuit, whether or not a control start motion is performed by the operator; and
validating, with the circuitry, a judgment result relating to the image switching motion if it is judged that the control start motion is performed.

15. The image control method according to claim 13, further comprising
judging, with the circuitry and based on the output from the detector circuit, whether or not an ultrasonic image switching motion is performed by the operator, wherein
the step of switching the endoscopic image data includes switching, if it is judged that the ultrasonic image switching motion is performed, the endoscopic image data output to the plurality of head-mounted displays to ultrasonic image data.

16. The image control method according to claim 13, further comprising:
judging, with the circuitry and based on the output from the detector circuit, whether or not a computer tomography (CT) image switching motion is performed by the operator; and
switching, with the circuitry and if it is judged that the CT image switching motion is performed, the endoscopic image data output to the plurality of head-mounted displays to CT image data.

17. The image control method according to claim 16, further comprising:
judging, with circuitry and based on the output from the detector circuit, whether or not a viewpoint changing motion is performed by the operator; and
switching, with the circuitry and if it is judged that the viewpoint changing motion is performed, image data output to the plurality of head-mounted displays to image data in which a viewpoint has been changed based on the viewpoint changing motion.

18. The image control method according to claim 13, further comprising:
judging, with circuitry and based on the output from the detector circuit, whether or not a magnification changing motion is performed by the operator; and
switching, with the circuitry and if it is judged that the magnification changing motion is performed, image data output to the plurality of head-mounted displays to image data in which a magnification of the image data is changed based on the magnification changing motion.

* * * * *

UNITED STATES PATENT AND TRADEMARK OFFICE
CERTIFICATE OF CORRECTION

PATENT NO. : 10,134,185 B2
APPLICATION NO. : 14/651415
DATED : November 20, 2018
INVENTOR(S) : Kazunori Kihara et al.

Page 1 of 1

It is certified that error appears in the above-identified patent and that said Letters Patent is hereby corrected as shown below:

On the Title Page

Item (71), the Applicant's information has been listed incorrectly. Item (71) should read:
-- (71) Applicant: SONY CORPORATION, Tokyo (JP) --

Signed and Sealed this
Twenty-eighth Day of May, 2019

Andrei Iancu
*Director of the United States Patent and Trademark Office*